US00PP11739P2

(12) United States Plant Patent
Schnitzler

(10) Patent No.: US PP11,739 P2
(45) Date of Patent: Jan. 9, 2001

(54) PEACH TREE NAMED 'KINGSBURG CLING'

(76) Inventor: Manfred Schnitzler, 14433 E. Stroud Ave., Kingsburg, CA (US) 93631

( * ) Notice: Under 35 U.S.C. 154(b), the term of this patent shall be extended for 0 days.

(21) Appl. No.: 09/150,394

(22) Filed: Sep. 9, 1998

(51) Int. Cl.[7] ..... A01H 5/00
(52) U.S. Cl. ..... Plt./197
(58) Field of Search ..... Plt./197

(56) References Cited

U.S. PATENT DOCUMENTS

P.P. 670 * 1/1946 Nicholson ..... Plt./197
P.P. 4,861 * 6/1982 Davis et al. ..... Plt./197
P.P. 11,090 * 10/1999 Zaiger et al. ..... Plt./197

OTHER PUBLICATIONS

Okie, W. R., Handbook of Peach and Nectarine Varieties USDA, ARS pp.77, 380, 446, 457, 776, May. 1998.*

* cited by examiner

*Primary Examiner*—Howard J. Locker
*Assistant Examiner*—Wendy A Baker
(74) *Attorney, Agent, or Firm*—Worrel & Worrel

(57) ABSTRACT

A new and distinct variety of peach tree which is somewhat similar to the 'Dr. Davis' peach tree (U.S. Plant Pat. No. 4,861), but from which it is distinguished by producing fruit which are mature for harvesting and shipment approximately two weeks prior to the fruit produced by the 'Dr. Davis' peach tree and wherein the fruit is of a more uniform quality.

1 Drawing Sheet

BACKGROUND OF THE NEW VARIETY

The present invention relates to a new and distinct variety of peach tree, which will hereinafter be denominated varietally as the Peach Tree Named 'Kingsburg Cling', *Prunus persica*, and, more particularly, to a peach tree which produces clingstone fruit, which are mature for commercial harvesting and shipment approximately July 15 to July 20 in the San Joaquin Valley of central California, which is two weeks earlier than the 'Dr. Davis' peach tree, and which possesses the texture, uniform color and firmness desired by the food processing industry as well as for other uses.

A variety of commercial markets exist for the use of tree fruit and considerable attention has been devoted to the development of tree fruit varieties well suited to particular markets. Thus, the fresh fruit market has seen extensive research and development over many decades in the invention or discovery of varieties well suited to the commercial use of fresh market fruit. The attributes of particular market importance in this regard include such considerations as maturity date, skin coloration, flavor, size and the like.

Another segment of the market which has seen perhaps less research and development of new varieties is that of the food processing industry. In this market, the desirable attributes vary to some degree depending upon the particular usage, or usages, to which the fruit is to be directed. For example, in canning of such tree fruit, such attributes as firmness, uniform skin coloration, uniform size and the like may be of most significant importance.

In the case of the canning industry, one of the more successful varieties of peach tree has been the 'Dr. Davis' peach tree (U.S. Plant Pat. No. 4,861). The fruit of this peach variety has been found well suited to use in the canning industry in many of the criteria heretofore set forth.

The instant variety of peach tree of the subject invention, while derived from the 'Dr. Davis' peach tree, is believed to be superior to that of its parent in a number of important respects relative to the food processing industry and particularly the canning segment of the industry. In addition, its maturity date differs from that of the 'Dr. Davis' peach tree and, therefore, is seen potentially to be a complement thereto.

ORIGIN AND ASEXUAL REPRODUCTION OF THE NEW VARIETY

The present variety of peach tree hereof was discovered by the inventor in about 1990 in his orchard which is located at 14433 E. Stroud Avenue, Kingsburg, Calif. in the San Joaquin Valley of central California. The inventor discovered the new variety, of the instant invention as a bud sport of the 'Dr. Davis' peach tree (U.S. Plant Pat. No. 4,861) in a five acre planting. Four trees were grafted from the bud sport onto 'Nemaguard' rootstock (unpatented) on the same property in 1991 and 1992. The asexually reproduced trees have been observed since that date, have borne fruit and the asexually reproduced trees have been observed to be identical in all respects.

SUMMARY OF THE NEW VARIETY

The Peach Tree Named 'Kingsburg Cling' is characterized by producing a clingstone fruit which has uniform coloration and is ripe for commercial harvesting and shipment approximately July 15 to July 20 in the San Joaquin Valley of central California. The new variety is most closely similar to the 'Dr. Davis' peach tree (U.S. Plant Pat. No. 4,861), but is distinguishable therefrom by the aforementioned ripening date. The fruit is clingstone, having a yellow flesh with red blush coloration, early maturity and is firm and somewhat sweet. These are attributes considered to be highly desirable for commercial processing. More specifically, the fruit of the new variety reaches maturity about two weeks earlier than the fruit of the parent variety. The fruit of the new variety has a yellow-orange skin coloration with a red blush on those areas of the fruit exposed to direct sunlight. In general, the fruit of the new variety possesses a skin coloration which is slightly more intense than the fruit of the parent variety. In summary, the fruit of the new variety has been observed to be superior to the fruit of the parent variety for purposes of commercial canning as well as for other purposes.

BRIEF DESCRIPTION OF THE DRAWING

The accompanying drawing is a color photograph of mature fruit of the new variety showing one in plan view showing the apex end thereof, a second sectioned along the suture and laid open with the stone removed to expose the pit well, a third in plan view showing the stem cavity thereof, a fourth sectioned so as to show representative flesh coloration and a fifth shown in side elevation showing the suture thereof; a stone of the new variety; and a portion of representative young growth and foliage. The colors illustrated are as close as it reasonably possible to obtain in a photographic illustration of this type.

DETAILED DESCRIPTION

Referring more specifically to the botanical details of this new and distinct variety of peach tree, the following has been observed under the ecological conditions prevailing at the orchard of origin which is located in Kingsburg, Calif. in the San Joaquin Valley of central California. All major color code designations are by reference to the Dictionary of Color, by Maerz and Paul, First Edition, published in 1930. Common color names are also occasionally employed.

TREE

Generally:

*Size.*—Medium to large.

*Vigor.*—Vigorous and hardy.

*Chilling Requirements.*—Normal for peach trees grown under the climatic conditions prevailing in the San Joaquin Valley of central California. Substantially the same as the 'Dr. Davis' peach tree (U.S. Plant Pat. No. 4,861), or about eight hundred fifty (850) hours.

*Figure.*—Upright growth habit.

*Productivity.*—Productive.

*Regularity of bearing.*—Regular.

Trunk:

*Size.*—Large in diameter.

*Surface texture.*—Somewhat coarse, younger bark is more smooth.

*Color.*—Oldest bark — (Pl. 14 K5).

*Color.*—Younger bark — (Pl. 15 L5) to (Pl. 15 L4).

*Lenticels.*—Numbers — Numerous.

*Lenticels.*—Size — Medium.

Branches:

*Size.*—Medium.

*Surface texture.*—Relatively smooth on both mature and immature growth.

*Color.*—One year or older wood — (Pl. 15 C3).

*Color.*—Immature branches — (Pl. 15 L4) to (Pl. 19 L4).

*Surface texture.*—Immature growth — Relatively smooth.

*Lenticels.*—Numbers — Few.

*Lenticels.*—Size — Medium.

Leaves:

*Size.*—Generally — Normal for peach foliage.

*Average length.*—100 mm (3.94 inches) to 112 mm (4.41 inches).

*Average width.*—25 mm (0.98 inch) to 36 mm (1.42 inches).

*Thickness.*—Average.

*Color.*—Upwardly disposed surface — (Pl. 21 L6).

*Color.*—Downwardly disposed surface — (Pl. 19 L8).

*Color.*—Leaf Vein — Mid — (Pl. 19 L5).

*Marginal form.*—Generally — Crenate.

*Leaf apex and leaf base.*—Acuminate.

*Leaf vein.*—Thickness — 4 mm (0.16 inch) to 6 mm (0.24 inch).

*Leaf margin.*—Serrate.

*Glandular characteristics.*—Reinform. One to four at base of leaf blade. May occur on both sides.

*Petiole.*—Size — Medium. 12 mm (0.47 inch to 15 mm (0.59 inch).

*Petiole.*—Length — 12 mm (0.47 inch) to 15 mm (0.59 inch).

*Petiole.*—Diameter — 6 mm (0.24 inch) to 7 mm (0.28 inch).

*Petiole.*—Thickness — 5 mm (0.2 inch).

*Petiole.*—Color — (Pl. 19 L5).

*Gland.*—Color — Green.

*Stipules.*—None.

*Peduncle.*—Short and thick.

*Peduncle.*—Size — Length — 4 mm (0.16 inch) to 5 mm (0.20 inch).

*Peduncle.*—Size — Diameter — 6 mm (0.24 inch) to 7 mm (0.28 inch).

Flowers:

*Flower buds.*—Size — 10 mm (0.39 inch). Plump with pointed end.

*Flower buds.*—Surface Texture — Glabrous.

*Date of bloom.*—February 25 (about 10%); March 2 (about 50%); March 12 (approximately 100%).

*Size.*—Diameter — 20 mm (0.79 inch) to 25 mm (0.98 inch).

*Petals.*—Color — Edges — (Pl. 53 9D).

*Petals.*—Color — Inside — (Pl. 53 J4).

*Petals.*—Number — Five. Non showy blossoms, fragrance lacking.

*Stamens.*—Size — Length — 20 mm (0.79 inch) to 25 mm (0.98 inches).

*Stamens.*—Color — (Pl. 21 J6).

*Pollination requirements.*—Self-fertile.

FRUIT

Maturity when described: Ripe for commercial harvesting and shipment approximately July 15 to July 20 in the climatic conditions prevailing in the San Joaquin Valley of central California.

Size:

*Generally.*—Globular in shape.

*Average diameter in the axial plane.*—67 mm (2.64 inches).

*Average diameter transverse in the suture plane.*—69 mm (2.72 inches).

*Average diameter transverse and at right angles to the suture plane.*—68 mm (2.68 inches).

*Form.*—Uniformity — Uniform, nearly equal on both halves.

*Form.*—Symmetry — Symmetrical.

*Suture.*—Generally — Shallow and extending from base to apex.

*Ventral surface.*—Generally — Distinctly lipped on most fruit.
*Stem cavity.*—Width — 8 mm (0.31 inch to 10 mm (0.39 inch).
*Stem cavity.*—Depth — 20 mm (0.79 inch) to 25 mm (0.98 inch).
*Stem cavity.*—Length — 10 mm (0.39 inch to 16 mm (0.63 inch).
*Stem cavity.*—Shape — Oval to round.
*Stem.*—Generally — Short.
*Stem.*—Caliper — 6 mm (0.24 inch) to 7 mm (0.28 inch).
*Apex.*—Shape — Rounded to slightly pointed.

Skin:
*Thickness.*—Average. The down, or fuzz, does not roll up — typical for a cling peach. Pubescence is short to medium.
*Texture.*—Firm at maturity.
*Tendency to crack.*—None observed.
*Bush color.*—(Pl. 3 K10), covers up to 50% of the fruit with most on the shoulders of the basal end.
*Ground color.*—(Pl. 11 K8).

Flesh:
*Flesh color.*—(Pl. 12 L8).
*Surface of pit cavity.*—Color — (Pl. 12 L11).
*Pit cavity.*—Color — (Pl. 12 L11).
*Juice production.*—Minimal.
*Flavor.*—Good for a clingstone peach.
*Aroma.*—Mild.
*Texture.*—Firm.
*Fibers.*—Numbers — Many.
*Fibers.*—Length — 15 mm (0.59 inch) to 20 mm (0.79 inch).
*Fibers.*—Texture — Relatively tender.
*Ripening.*—Even.
*Eating quality.*—Good for processed fruit such as used by the canning industry.

Stone:
*Attachment.*—Clingstone.
*Fibers.*—Numbers — Many.
*Fibers.*—Length — 15 mm (0.59 inch) to 20 mm (0.79 inch).
*Size.*—Length — 30 mm (1.18 inches) to 37 mm (1.46 inches).
*Size.*—Width — 24 mm (0.94 inch) to 27 mm (1.06 inches).
*Size.*—Thickness — 18 mm (0.71 inch).
*Form.*—Generally — Globose.
*Apex.*—Shape — Slightly pointed.
*Color.*—Dry — (Pl. 12 L7).
*Base.*—Shape — Slightly rounded.
*Sides.*—Generally — Smooth, unequal slightly.
*Ridges.*—On both sides, parallel to edge from base to apex.
*Dorsal edge.*—Rounded in shape, moderately wide grooves from base to apex.
*Ventral edge.*—Slightly raised wings at basal end.
*Tendency to split.*—None.

Use: for commercial harvesting and food processing. Is expected to be of particular utility in the canning industry.
Canning quality: Excellent.
Keeping quality: Very good.
Resistance to disease: No unusual susceptibility to disease has been noted.
Harvesting: Commercially July 15 to July 20 in the San Joaquin Valley of central California.
Shipping and handling qualities: Very good.

Although the new variety of peach tree possesses the described characteristics noted above as a result of the growing conditions prevailing in Kingsburg, Calif. in the San Joaquin Valley of central California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by Plant Letters Patent is:

1. A new and distinct variety of peach tree substantially as illustrated and described herein.

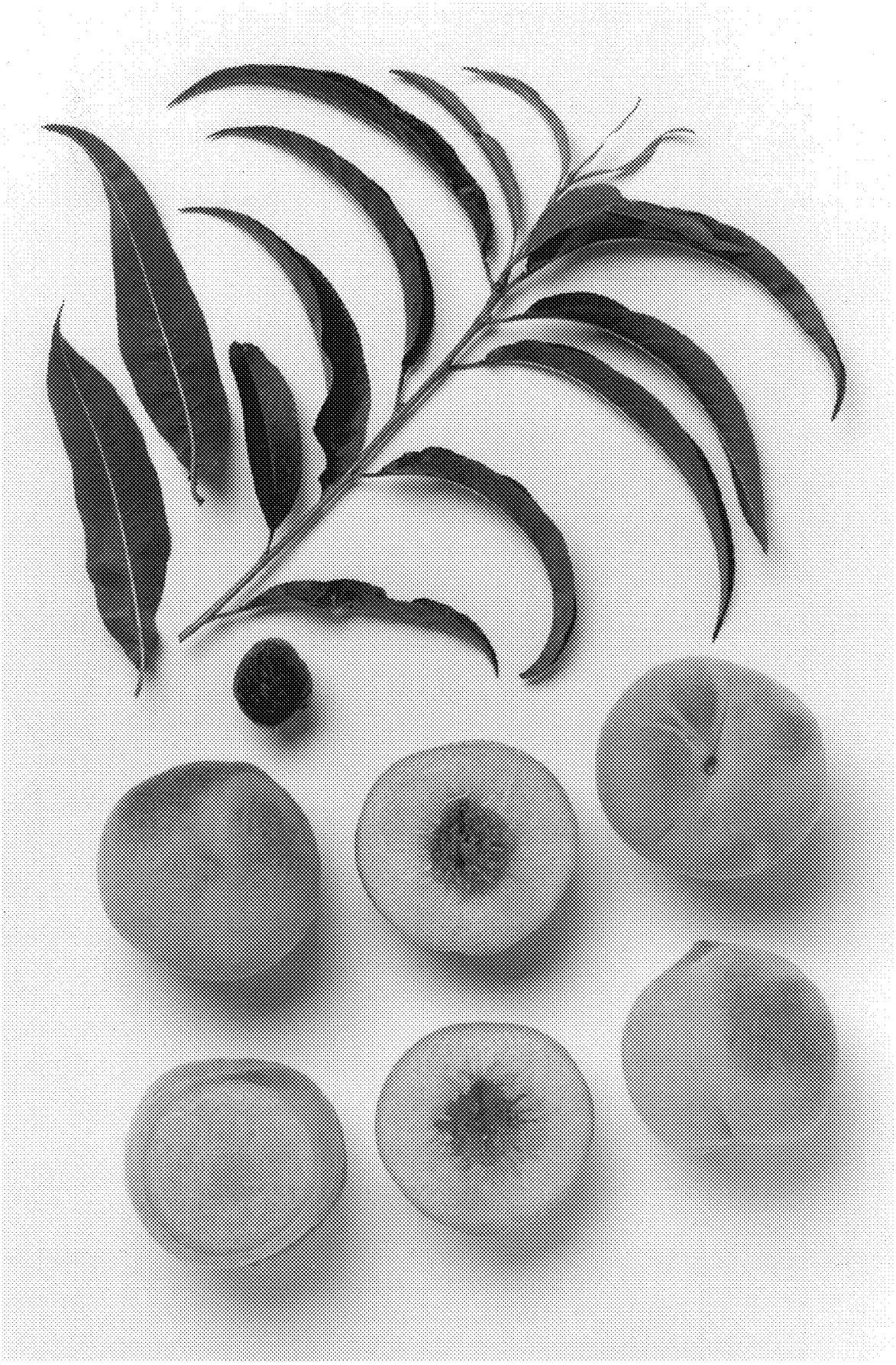

* * * * *